(12) United States Patent
Clements et al.

(10) Patent No.: US 9,861,670 B2
(45) Date of Patent: Jan. 9, 2018

(54) STABILIZED CREAM FORMULATIONS COMPRISING SANDALWOOD OIL

(71) Applicant: ViroXis Corporation, San Antonio, TX (US)

(72) Inventors: Ian Clements, San Antonio, TX (US); Paul Castella, San Antonio, TX (US); Corey Levenson, San Antonio, TX (US)

(73) Assignee: SANTALIS HEALTHCARE CORPORATION, San Antonio, TX (US)

( * ) Notice: Subject to any disclaimer, the term of this patent is extended or adjusted under 35 U.S.C. 154(b) by 0 days.

(21) Appl. No.: 14/773,127

(22) PCT Filed: Mar. 13, 2014

(86) PCT No.: PCT/US2014/026219
§ 371 (c)(1),
(2) Date: Sep. 4, 2015

(87) PCT Pub. No.: WO2014/160279
PCT Pub. Date: Oct. 2, 2014

(65) Prior Publication Data
US 2016/0008415 A1    Jan. 14, 2016

Related U.S. Application Data

(60) Provisional application No. 61/780,038, filed on Mar. 13, 2013.

(51) Int. Cl.
| *A61K 36/185* | (2006.01) |
| *A61K 36/53* | (2006.01) |
| *A61K 31/05* | (2006.01) |
| *A61K 9/00* | (2006.01) |
| *A61K 9/06* | (2006.01) |
| *A61K 45/06* | (2006.01) |
| *A61K 31/122* | (2006.01) |
| *A61K 9/107* | (2006.01) |

(52) U.S. Cl.
CPC .......... *A61K 36/185* (2013.01); *A61K 9/0014* (2013.01); *A61K 9/06* (2013.01); *A61K 31/05* (2013.01); *A61K 31/122* (2013.01); *A61K 36/53* (2013.01); *A61K 45/06* (2013.01); *A61K 9/107* (2013.01)

(58) Field of Classification Search
CPC ...................................................... A61K 36/18
USPC ................................................. 424/725, 775
See application file for complete search history.

(56) References Cited

U.S. PATENT DOCUMENTS

| 5,520,918 A | 5/1996 | Smith et al. |
| 5,653,970 A | 8/1997 | Vermeer |
| 5,693,327 A | 12/1997 | Shah |
| 5,944,754 A | 8/1999 | Vacanti |
| 6,132,756 A | 10/2000 | Haque et al. |
| 6,368,639 B1 | 4/2002 | Farooqi et al. |
| 6,406,706 B1 | 6/2002 | Haque et al. |
| 6,576,269 B1 | 6/2003 | Korneyev et al. |
| 7,858,126 B2 * | 12/2010 | Singh .................. A61K 31/215 424/725 |
| 2005/0158258 A1 | 7/2005 | Fisher |
| 2006/0058238 A1 | 3/2006 | Laurent-Applegate et al. |
| 2007/0166275 A1 | 7/2007 | Gan et al. |
| 2009/0047372 A1 | 2/2009 | Miller |
| 2009/0068128 A1 | 3/2009 | Waddington |
| 2009/0274677 A1 | 11/2009 | Isaacs et al. |
| 2010/0029766 A1 | 2/2010 | Barclay et al. |
| 2010/0226983 A1 | 9/2010 | Sutcliffe et al. |
| 2010/0303854 A1 | 12/2010 | Hines et al. |
| 2013/0005830 A1 | 1/2013 | Clements et al. |
| 2014/0154342 A1 | 6/2014 | Clements et al. |

FOREIGN PATENT DOCUMENTS

| CN | 101370508 A | 2/2009 |
| CN | 103181937 A | 7/2013 |
| EP | 1059086 A1 | 12/2000 |
| EP | 1402785 A1 | 3/2004 |
| EP | 2181690 | 5/2010 |
| GB | 2309902 A | 8/1997 |
| JP | 58225199 | 12/1983 |
| JP | 63199292 | 8/1988 |
| JP | 2001322943 | 11/2001 |
| JP | 2006124296 A | 5/2006 |

(Continued)

OTHER PUBLICATIONS

Database WPI Week 200636 Thomson Scientific, London, GB; AN 2006-347100 XP002707361, & JP 2006 124296 A.
Mohammed Azam Khan; Ikseer Azam, vol. IV (19th century AD), Matba Nizami Kanpur, 1872 AD, p. 309 (Formulation ID: BA4/1854B; Marham Baraa-e-Sartaan).
Mohammed Azam Khan; Ikseer Azam, vol. IV (19th century AD), Matba Nizami Kanpur, 1872 AD, p. 309, (Formulation ID: BA4/1854C; Tila), 1872, 2 pages.
Mohammed Akbar Arzani; Qaraabaadeen Qaadri (17th century AD), Ahmadi Publication, Delhi, 1968, p. 422.
Rasatantrasarah Evam Siddhaprayogasamgrahah; part II; Krishnan Gopal Ayurveda Bhawan; Edn 8th, 1990, 3 pages.

(Continued)

*Primary Examiner* — Chris R Tate
*Assistant Examiner* — Deborah Davis
(74) *Attorney, Agent, or Firm* — Kilpatrick Townsend & Stockton LLP

(57) ABSTRACT

Provided herein are cream formulations comprising sandalwood oil, an antioxidant and a phosphate buffer. Also provided are methods of making and using the formulations. Further provided herein is a method of treating a skin disorder in a subject by administering to the subject a therapeutically effective amount of a cream formulation comprising sandalwood oil, an antioxidant and a phosphate buffer, wherein the subject has a skin disorder or is at risk of developing a skin disorder.

14 Claims, 2 Drawing Sheets

(56) References Cited

FOREIGN PATENT DOCUMENTS

| | | |
|---|---|---|
| JP | 2009057325 A | 3/2009 |
| WO | 2007084998 A2 | 7/2007 |
| WO | 2010087964 A2 | 8/2010 |
| WO | 2010091415 A1 | 8/2010 |
| WO | 2011002929 A1 | 1/2011 |
| WO | 2013112582 A1 | 8/2013 |

OTHER PUBLICATIONS

Swami Harisaranananda Vaidya; Asava Vijnan-translated by Swami Harisaranananda Vaidya, published by the Punjab Ayurvedic Pharmacy, Amritsar, 3rd edition, 2000, 4 pages.

Abdulla Sahib; Anuboga Vaithya Navaneetham, Part 6; Ed: Mohammed Abdulla Shahib, Publisher: Thamarai Noolagam, Chennai, 2001, pp. 47-48.

http://www.viroxis.com/science.html, 2012, 2 pages.

"A medicated core of bra having anticancer and breast beautifying effects and its preparation method", TCM/SIPO, XP-002707360, Sep. 15, 1992, 4 pages.

"Madhana Kameswara Thylam", Key Attributes to TKDL, 4 pages.

U.S. Appl. No. 14/235,387, "Advisory Action", dated Mar. 24, 2016, 3 pages.

U.S. Appl. No. 14/235,387, "Final Office Action", dated Sep. 4, 2015, 14 pages.

U.S. Appl. No. 14/235,387, "Non-Final Office Action", dated Dec. 3, 2014, 17 pages.

AU2012286671, "First Examiner Report", dated Jul. 20, 2016, 3 pages.

Banerjee, et al., "Modulatory influence of sandalwood oil on mouse hepatic glutathione S-transferase activity and acid soluble sulphydryl level", level, Cancer Letters, 68, 1993, pp. 105-109.

Burdock, et al., "Safety Assessment of Sandalwood Oil (*Santalum album* L.)", Food and Chemical Toxicology, vol. 46, 2008, pp. 421-432.

CN201280044415.8, "Office Action with English Translation", dated Dec. 29, 2015.

CN201280044415.8, "Office Action with English Translation", dated Mar. 2, 2015.

CN201280044415.8, "Office Action with English Translation", dated May 27, 2016.

Dwivedi, et al., "Chemopreventive Effects of Sandalwood Oil on Skin Papillomas in Mice", European Journal of Cancer Prevention, vol. 6, No. 4, Aug. 1997, pp. 399-401.

EP11751210.3, "Communication pursuant to Rule 114(2) EPC including third party observations under Article 115 EPC", Sep. 10, 2013, 9 pages.

EP11751210.3, "Extended European Search Report", dated Aug. 22, 2013, 10 pages.

EP12818159.1, "Extended European Search Report", dated Feb. 3, 2015, 7 pages.

EP14775788.4, "Extended European Search Report", dated Aug. 19, 2016, 6 pages.

Erligmann, et al., "Sandalwood Oils", The International Journal of Aromatherapy, vol. 11, No. 4, 2001, pp. 186-192.

Hayes, et al., "Toxicity of Australian essential oil Backhousia citriodora (Lemon myrtle). Part 1. Antimicrobial activity and in vitro cytotoxicity", Food and Chemical Toxicology, 2002, pp. 535-543.

Hettiarachchi, et al., "Western Australian sandalwood seed oil: new opportunities", Lipid Technology, vol. 22, No. 2, Feb. 2010, pp. 27-29.

JP2014-523078, "Office Action with English Translation", dated Jun. 6, 2016.

Kaur, et al., "Skin cancer chemopreventive agent; a-santalol, induces apoptotic death of human eptdermmd carcmoma A431 cells vaa caspase activation together with dissipation of mitochondrial membrane potential and cytochrome c release", Carcinogenesis, vol. 26, No. 2, XP-002593567, doi: 10.1093/carcin/bgh325, 2005, pp. 369-380.

Panda, "The Complete Technology Book on Herbal Perfumes & Cosmetics. National Institute of Industrial Research", 2003, 169-170.

PCT/US2011/026706, "International Preliminary Report on Patentability", dated Sep. 4, 2012.

PCT/US2012/048599, "International Preliminary Report on Patentability", dated Jan. 28, 2014, 5 pages.

PCT/US2012/048599, "International Search Report and Written Opinion Received", dated Nov. 15, 2012, 8 pages.

PCT/US2014/026219, "International Preliminary Report on Patentability", dated Sep. 24, 2015, 8 pages.

PCT/US2014/026219, "International Search Report and Written Opinion", dated Jul. 10, 2014, 11 pages.

Raju, et al., "Formulation and evaluation of oral and topical preparations using natural products", Journal of Natural Pharmaceuticals, vol. 4, No. 1, 2013, pp. 37-47.

Sindhu, et al., "Santalum Album Linn: A Review on Morphology, Phytochemistry and Pharmacological Aspects", International Journal of PharmTech Research, vol. 2, No. 1, Jan.-Mar. 2010, pp. 914-919.

Va Gasena, 12th Century—commentator Shaligram Vaisya, Edited Shankar Ialji Jain; Khemraj Shrikrishna Das Prakashan, Bombay, Edn. TKDL identifier AK11/3505, 1996, 2 pages.

Vettian, 10-15th Century A.D., Ed: Mangadu Vadivel Mudalia, Pub: Parthina Nayakar & sons, Thirumagal Vilakku press, Chennai, TKDL identifier GP11/20, pp. 272-278.

Australian Patent Application No. 2011223758, Patent Examination Report No. 1, dated Jan. 27, 2015, 4 pages.

Japanese Patent Application No. JP2012-556177, Office Action and English translation, dated Feb. 24, 2015, 5 pages.

U.S. Appl. No. 13/582,133, Final Office Action, dated Apr. 22, 2014, 13 pages.

U.S. Appl. No. 13/582,133, Non-Final Office Action, dated Oct. 18, 2013, 11 pages.

U.S. Appl. No. 13/582,133, Notice of Panel Decision, dated Oct. 29, 2014, 2 pages.

U.S. Appl. No. 14/235,387, Non Final Office Action, dated Nov. 14, 2016, 24 pages.

Boris et al., "Cytotoxic Properties of Selected Sesquiterpene Alcohols on Human Cervix Carcinoma Cell Lines", Journal of Essential Oil Bearing Plants, vol. 14, Issue 3, 2011, pp. 316-319.

EP12818159.1 , Office Action, dated Mar. 21, 2017, 4 pages.

Lee et al., "Effects of Natural Products on the Inhibition of 5a-Reductase Type 2 for the Development of Chemopreventive Agents in LNCaP Cells", Natural Product Sciences, 5(s), 1999, pp. 97-103.

Takatsuki et al., "Studies on Cytotoxic Activity of Animal and Plant Crude Drugs", Natural Medicines, pp. 50(2), 1996, pp. 145-157.

Azam , vol. IV (19th century AD), Matba Nizami Kanpur, 1872 AD, p. 309, (Formulation ID: BA4/1854C; Tila), 1872, p. 309.

Chinese Patent Application No. 201280044415.8, Office Action and English translation, dated Jun. 13, 2017, 6 pages.

Japanese Patent Application No. 2014-523078, Office Action and English translation, dated Mar. 30, 2017, 17 pages.

Product Catalogue 2010, "Aloe Vera Cosmetics Australia Pty Ltd", http://www.aloeveracosmetics.com.au/pdf/AVCA-Catalogue-2010.pdf, 2010, 22 pages.

CN201280044415.8, "Notice of Decision to Grant", Oct. 11, 2017, 4 pages.

JP2016-502077, "Office Action" with English translation, Oct. 2, 2017, 16 pages.

\* cited by examiner

STABILIZED CREAM FORMULATIONS COMPRISING SANDALWOOD OIL

This application claims the benefit of U.S. Application No. 61/780,038, filed on Mar. 13, 2013, which is hereby incorporated in its entirety by this reference.

SUMMARY

Provided herein are cream formulations comprising sandalwood oil, an antioxidant and a phosphate buffer. Also provided are methods of making and using the formulations. Further provided herein is a method of treating a skin disorder in a subject by administering to the subject a therapeutically effective amount of a cream formulation comprising sandalwood oil, an antioxidant and a phosphate buffer, wherein the subject has a skin disorder or is at risk of developing a skin disorder.

DETAILED DESCRIPTION

Figure 1:
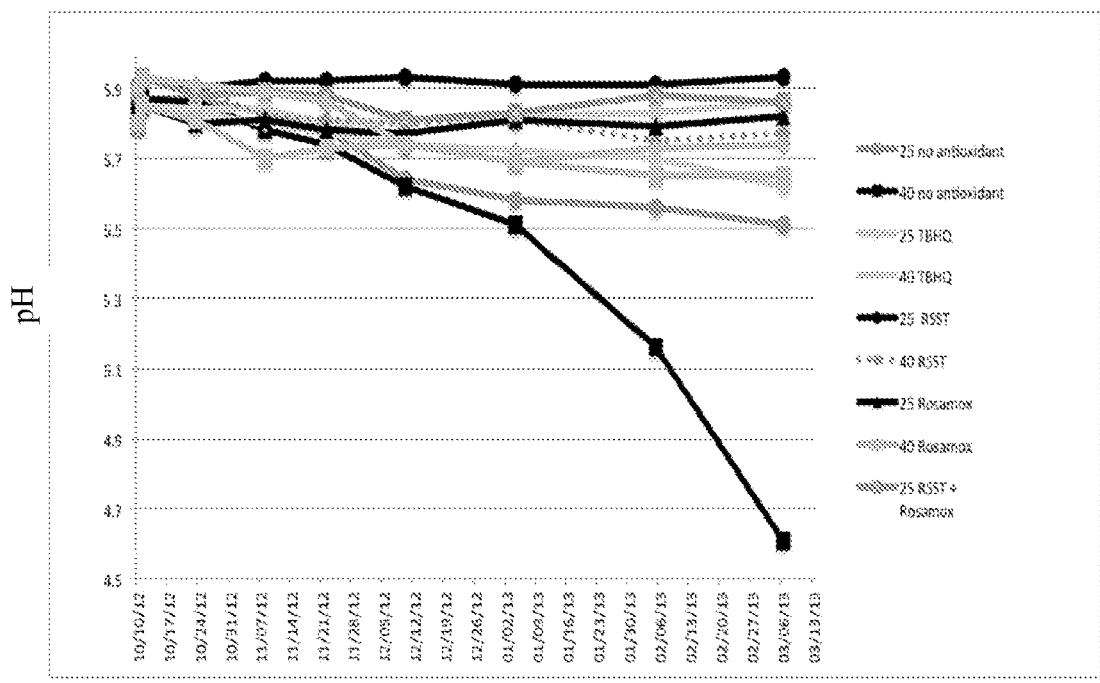
FIG. 1 is a graph showing the decrease in pH at 25° C. and at 40° C. for a cream formulation that does not comprise an antioxidant vs. the stable pH observed at 25° C. and at 40° C. for cream formulations comprising sandalwood oil and an antioxidant. This graph represents the data shown in Tables 3-7.

In the present compositions and methods, oil from any member of the genus Santalum can be used. For example, and not to be limiting, East Indian sandalwood (Santalum album) or West Australian sandalwood (Santalum spicatum) can be utilized in any of the methods and compositions set forth herein. Several other members of the genus species also have fragrant wood and are found across India, Australia, Indonesia, and the Pacific Islands. Santalum ellipticum, S. freycinetianum, and S. paniculatum, the Hawaiian sandalwoods, can also be used. Rectified East Indian Sandalwood Oil from Australian Grown Trees (PISO) can also be used.

As set forth above, Santalum spicatum (West Australian sandalwood) can be used. Other species produced in Australia that can be utilized in the methods and compositions set forth herein include, but are not limited to, S. acuminatum, S. lanceolatum, S. murrayanum, S. obtusifolium and S. album. The compositions set forth herein can comprise one or more sandalwood oils. The oil(s) can be from one or more members of the genus Santalum. The sandalwood oil can be sandalwood heartwood oil.

The components of S. spicatum and S. album species are different. A comparison of the components of steam distilled Australian and Indian sandalwood oils is presented in

TABLE 1

The components and their percentages can vary with the extraction method.
Table 1: Typical Sandalwood Heartwood Oil Profiles

| Compound | S. spicatum % | S. album % |
|---|---|---|
| E nerolidol | 2.1% | 0.1% |
| Alpha-santalene | nd | 0.5% |

TABLE 1-continued

The components and their percentages can vary with the extraction method.
Table 1: Typical Sandalwood Heartwood Oil Profiles

| Compound | S. spicatum % | S. album % |
|---|---|---|
| Cis-alpha-(trans) bergamotene | nd | 0.7% |
| Epi-beta-santalene | nd | 1.1% |
| Beta-santalene | nd | 0.3% |
| Gamma-curcumene | nd | 0.2% |
| Dendrolasin | 1.2% | 0.2% |
| Alpha-santalol | 17.2% | 48.7% |
| Beta-bisabolol | 2.3% | 0.5% |
| Epi -alpha-bisabolol | 8% | nd |
| Z-alpha trans -bergamotol | 4.2% | 2.4% |
| Epi beta -santalol | 1.2% | 5% |
| Cis -beta-santalol | 11.4% | 20.4% |
| E,E, farnesol | 6.5% | nd |
| Cis nuciferol | 13.5% | 0.6% |
| Z-beta-curcumen-12-ol | 7.9% | 0.2% |
| cis lanceol | 2.9% | 1.5% |

The sandalwood oil can be prepared by steam distillation, supercritical $CO_2$ extraction, solvent extraction, hydro-distillation and combinations thereof. The sandalwood oil can also be double distilled. It is also possible to synthesize one or more of the active ingredients of sandalwood heartwood oil, as identified in Table 1 and thereafter combine individual active ingredients together.

As used herein, a sandalwood oil can be a sandalwood oil that conforms with International Organization for Standardization (ISO) specifications for the oil and therefore comprises 20-45% santalols, when derived from S. spicatum, and 57-79% santalols when derived from S. album. However, the 20-45% santalols and the 57-79% santalols are determined against the pure oil and before such oil is combined with any other solvents, excipients or active ingredients. It is understood that an efficacious preparation of sandalwood oil may have a concentration of santalols lower (or higher) than the sandalwood oil it is prepared from, and that the efficacious concentrations may be derived from sandalwood oils that are outside of the ISO specification prior to formulation. A santalol can be an α-santalol (shown below), a β-santalol (shown below), or any other active isomers or derivatives (such as esters) thereof.

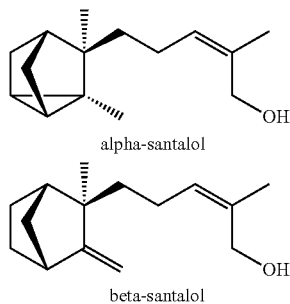

alpha-santalol beta-santalol

As used herein, a sandalwood oil can comprise at least about 20%, 25%, 30%, 35%, 40%, 45%, 50%, 55%, 60%, 65%, 70%, 75%, 80%, 85%, 90%, 95%, or 99% santalols or any percentage in between the percentages set forth herein, when derived from S. spicatum. The sandalwood oil can comprise at least about 45%, 50%, 55%, 60%, 65%, 70%, 75%, 80%, 85%, 90%, 95%, or 99% santalols or any percentage in between the percentages set forth herein, when derived from *S. album*. The oil can be extracted from cultivated trees or from cell culture of tree cells.

In the methods and compositions set forth herein, the sandalwood oil can comprise the ingredients in the amounts listed in Table 1 plus or minus about 20%, and more preferably plus or minus about 10%, 5%, 2%, 1% or any percentage in between the percentages set forth herein.

It is also understood that the activity of sandalwood oil can be due to one or more components set forth in Table 1 acting either separately or together. Therefore, formulations that increase the concentration of the active component(s) and reduce the concentration of the inactive component(s) are set forth herein. Synthetic versions of the active components, or their derivatives, may be formulated in conjunction with or to replace the naturally occurring components of sandalwood oil.

Provided herein are cream formulations comprising sandalwood oil, an antioxidant and a phosphate buffer. These cream formulations exhibit stable pH, over time, at temperatures ranging from about 25° C. to about 40° C., as compared to cream formulations comprising sandalwood oil, wherein the formulation does not comprise an antioxidant (i.e., is relatively devoid of antioxidants). For example, these formulations exhibit stable pH for one month, two months, three months, four months, five months, six months, seven months, eight months, nine months, ten months, eleven months, a year or more after the formulation is made. These formulations also withstand discoloration. The sandalwood oil in these formulations can be present in a therapeutically effective amount. Therefore, provided herein are therapeutically effective cream formulations comprising sandalwood oil, an antioxidant and a phosphate buffer.

As utilized herein, a therapeutically effective amount of sandalwood oil is an amount that is sufficient to reduce the effects of a skin disorder or a symptom of a skin disorder. The therapeutically effective amount of sandalwood heartwood oil utilized in the compositions set forth herein can be, for example, a concentration greater than about 0.3% (w/w) and up to about 70% (w/w). For example, the therapeutically effective amount can be about 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0%, 10.1%, 10.2%, 10.3%, 10.4%, 10.5%, 10.6%, 10.7%, 10.8%, 10.9%, 11.0%, 11.1%, 11.2%, 11.3%, 11.4%, 11.5%, 11.6%, 11.7%, 11.8%, 11.9%, 12.0%, 12.1%, 12.2%, 12.3%, 12.4%, 12.5%, 12.6%, 12.7%, 12.8%, 12.9%, 13.0%, 13.1%, 13.2%, 13.3%, 13.4%, 13.5%, 13.6%, 13.7%, 13.8%, 13.9%, 14.0%, 14.1%, 14.2%, 14.3%, 14.4%, 14.5%, 14.6%, 14.7%, 14.8%, 14.9%, 15.0%, 20%, 25%, 30%, 35% 40%, 45%, 50%, 55%, 60%, 65%, 70% or any percentage (w/w) in between the percentages set forth herein.

The therapeutically effective amount of sandalwood oil can also be from about 1.0% to about 3%, from about 1.0% to about 5.0%, from about 1.0% to about 7.5%, from about 1.0% to about 10.0%, from about 1.0% to about 15.0%, from about 2.0% to about 3%, from about 2.0% to about 5.0%, from about 2.0% to about 7.5%, from about 2.0% to about 10.0%, from about 2.0% to about 15.0%, from about 3.0% to about 5.0%, from about 3.0% to about 7.5%, from about 3.0% to about 10.0%, from about 3.0% to about 15.0%, from about 4.0% to about 5.0%, from about 4.0% to about 7.5%, from about 4.0% to about 10.0%, from about 4.0% to about 15.0%, from about 5.0% to about 7.5%, from about 5.0% to about 10.0% or from about 5.0% to about 15% (w/w), from about 10% to about 15%, from about 10% to about 20%, from about 10% to about 30%, from about 10% to about 40%, from about 10% to 50%, from about 10% to about 60%, from about 10% to about 70%, from about 20% to about 30%, from about 20% to about 40%, from about 20% to about 50%, from about 20% to about 60%, from about 20% to about 70%, from about 30% to about 40%, from about 30% to about 50%, from about 30% to about 60%, from about 30% to about 70%, from about 40% to about 50%, from about 40% to about 60%, from about 40% to about 70%, from about 50% to about 60%, from about 50% to about 70% or from about 60% to about 70%. One of skill understands that the other components in the formulation, for example, the antioxidant and the phosphate buffer can be adjusted as the amount of sandalwood oil in the formulation increases.

The formulations provided herein comprise an antioxidant. The antioxidant can be selected from the group consisting of t-butyl hydroquinone (TBHQ), Rosamox and Botanessentials RSST. One or more antioxidants selected from the group consisting of t-butyl hydroquinone (TBHQ), Rosamox and Botanessentials RSST can be used in the formulations provided herein. Other antioxidants can be used and will be known to those of skill in the art. For example, and not to be limiting, one or more of α-tocopherol, beta-carotene, butylated hydroxyanisole (BHA), butylated hydroxytoluene (BHT), caffeic acid, lutein, lycopene, selenium, Vitamin A, Vitamin C, and Vitamin E can be used as antioxidants. Further examples of suitable antioxidants include putative antioxidant botanicals, such as, for example, grape seeds, green tea, *Scutellaria baicalensis*, American *ginseng, ginkgo biloba*, and the like.

The concentration of the antioxidant can be from about 0.03% (w/w) to about 3% (w/w), for example, from about 0.03% (w/w) to about 0.1% (w/w), from about 0.03% (w/w) to about 0.2% (w/w), from about 0.03% (w/w) to about 0.3% (w/w), 0.03% (w/w) to about 0.4% (w/w), from about 0.03% (w/w) to about 0.5% (w/w), from about 0.03% (w/w) to about 0.6% (w/w), from about 0.03% (w/w) to about 0.7% (w/w), from about 0.03% (w/w) to about 0.8% (w/w), from about 0.03% (w/w) to about 0.9% (w/w), from about 0.03% (w/w) to about 1.0% (w/w), from about 0.03% (w/w) to about 1.5% (w/w), from about 0.03% (w/w) to about 2.0% (w/w), from about 0.03% (w/w) to about 2.5% (w/w), from about from about 0.03% (w/w) to about 3.0% (w/w). For example, the concentration can be about 0.05%, 0.055%, 0.06%, 0.065% 0.07%, 0.075%, 0.08%, 0.085%, 0.09%, 0.095%, 0.1%, 0.15%, 0.2%, 0.25%, 0.3%, 0.35%, 0.4%, 0.45%, 0.5%, 0.55%, 0.6%, 0.65%. 0.7%. 0.75%. 0.8%, 0.85%, 0.9%, 0.95%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0% or any percentage (w/w) in between the percentages set forth herein. In another example, the concentration of TBHQ can be from about 0.03% (w/w) to about 0.1% (w/w). For example, the concentration of TBHQ can be about 0.03%, 0.04%, 0.05%, 0.06%, 0.07%, 0.08%, 0.09%, 0.1% or any percentage (w/w) in between the percentages set forth herein. In another example, the concentration of Rosamox can be from about 0.1% (w/w) to about 1% (w/w). For example, the concentration of Rosamox can be about 0.1%, 0.15%, 0.2%, 0.25%, 0.3%, 0.35%, 0.4%, 0.45%, 0.5%, 0.55%, 0.6%, 0.65%. 0.7%. 0.75%. 0.8%, 0.85%, 0.9%, 0.95%, 1.0% or any percentage (w/w) in between the percentages set forth herein. In a formulation comprising Botanessentials RSST, the concentration of Botanessentials RSST can be from about 0.5% (w/w) to about 3% (w/w). For example, the concentration of Botanessentials RSST can be about 0.5%, 0.55%, 0.6%, 0.65%. 0.7%. 0.75%. 0.8%, 0.85%, 0.9%, 0.95%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0% or any percentage (w/w) in between the percentages set forth herein.

The formulations set forth herein also comprise a phosphate buffer. The phosphate buffer can be, for example, potassium phosphate monobasic or potassium phosphate dibasic. Other phosphate, citrate and acetate buffers can be used. Other buffers include, but are not limited to, MES, Bis-Tris, ADA, aces, PIPES, MOPSO, Bis-Tris-Propane, BES, MOPS, TES, HEPES DIPSO, MOBS, TAPSO, Trizma, HEPPSO, POPSO, TEA, EPPS, Tricine, Gly-Gly, Bicine, HEPBS, TAPS, AMPD, TABS, AMPSO, CHES, CAPSO, AMP, CAPS or CABS. The concentration of the buffer, for example, a phosphate buffer, should be sufficient to maintain the pH of the formulation between 4 and 6. The concentration of the buffer, for example, a phosphate buffer, should also be sufficient to maintain the pH of the formulation over time, for example, from about one month to about six months, or from about one month to about a year or more, at a temperature ranging from about 25° C. to about 40° C. The concentration of the phosphate buffer can range from about 0.05% to about 10% (w/w). For example, the concentration can be about 0.05%, 0.055%, 0.06%, 0.065% 0.07%, 0.075%, 0.08%, 0.085%, 0.09%, 0.095%, 0.1%, 0.15%, 0.2%, 0.25%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0%, or any percentage (w/w) in between the percentages set forth herein.

The compositions set forth herein can include one or more solvents, including, but not limited to, a solvent(s) selected from the group consisting of water, alcohol, glycol, glycerol, glycerine, octoxyglycerin, diglycerol, butylene glycol, propylene glycol, dipropylene glycol, and vegetable oils. Examples of alcohols include but are not limited to methanol, ethanol, n-propanol, isopropyl alcohol, 2-methyl-2 propanol, hexanol, or combinations thereof. Aromatic alcohols, for example, phenoxy ethanol, benzyl alcohol, 1-phenoxy-2-propanol, and/or phenethyl alcohol can also be used. The solvent concentration can range from about 3% to about 90% (w/w), for example, from about 3% to about 90%, from about 5% to about 90%, from about 10% to about 90% (w/w) or from about 20% to about 90% (w/w). For example, the concentration of the solvent can be about 3%, 5%, 10%, 15%, 20%, 25%, 30%, 35%, 40%, 45%, 50%, 55%, 60%, 65%, 70%, 75%, 80%, 85%, 90% or any percentage (w/w) in between the percentages set forth herein.

The formulations set forth herein can further comprise a pharmaceutically acceptable carriers or excipients. Other ingredients can also be included in the compositions set forth herein, which can be selected from skin cleansers, vitamins, hormones, minerals, anti-inflammatory agents, collagen and elastin synthesis boosters, UVA/UVB sunscreens, emollients, moisturizers, skin protectants, humectants, silicones, skin soothing ingredients, moisture absorbents, a powder, skin penetration enhancers, emulsifiers, solubilizers, thickeners, gelling agents, colorants, perfumes, preservatives, silica, clays, beads, luffa particles, polyethylene balls, mica, processing aids, and combinations thereof. The compositions can further comprise other excipients such as hydroxypropylmethyl cellulose, cationic hydroxyethyl cellulose, ethyl cellulose, hydroxypropyl cellulose, hydroxymethyl cellulose, carboxy methyl cellulose, polyethylene oxide (polyox resins), and chitosan pyrrolidone carboxylate.

Examples of emollients include, but are not limited to, PEG 20 almond glycerides, Probutyl DB-IO, Glucam P-20, Glucam E-IO, Glucam P-10, Glucam E-20, Glucam P-20 distearate, glycerin, propylene glycol, octoxyglycerin, cetyl acetate, acetylated lanolin alcohol (e.g., Acetulan), cetyl ether (e.g., PPG-10), myristyril ether (e.g., PPG-3), hydroxylated milk glycerides (e.g., Cremeral HMG), polyquaternium compounds, copolymers of dimethyl dialyl ammonium chloride and acrylic acid (e.g., Merquat), dipropylene glycol methyl ethers (e.g., Dowanol DPM, Dow Corning), polypropylene glycol ethers and silicon polymers. Other suitable emollients may include hydrocarbon-based emollients such as petrolatum or mineral oil, fatty ester-based emollients, such as methyl, isopropyl and butyl esters of fatty acids such as isopropyl palmitate, isopropyl myristate, isopropyl isostearate, isostearyl isostearate, diisopropyl sebacate, and propylene dipelargonate, 2-ethylhexyl isononoate, 2-ethylhexyl stearate, cetyl lactate, lauryl lactate, isopropyl lanolate, 2-ethylhexyl salicylate, cetyl myristate, oleyl myristate, oleyl stearate, oleyl oleate, hexyl laurate, and isohexyl laurate. Other moisturizers include, but are not limited to, lanolin, olive oil, cocoa butter, and shea butter.

The concentration of the excipient(s) can range from about 1.0% to about 90% (w/w), including, for example, from about 5% to about 90% (w/w), from about 10% to about 90% (w/w) or from about 20% to about 90% (w/w).

For example, the concentration of the excipient can be about 1%, 2%, 3%, 4%, 5%, 10%, 15%, 20%, 25%, 30%, 35%, 40%, 45%, 50%, 55%, 60%, 65%, 70%, 75%, 80%, 85%, 90% or any percentage (w/w) in between the percentages set forth herein. It is also understood that the combined concentration of the solvent(s) and excipient(s) can range from about 1% to about 90% (w/w), including, for example, from about 5% to about 90% (w/w), from about 10% to about 90% (w/w) or from about 20% to about 90% (w/w). For example, the combined concentration of the solvent(s) and excipient(s) can be about 1%, 3%, 5%, 10%, 15%, 20%, 25%, 30%, 35%, 40%, 45%, 50%, 55%, 60%, 65%, 70%, 75%, 80%, 85%, 90% or any percentage (w/w) in between the percentages set forth herein.

Any of the compositions set forth herein can be used to treat a skin disorder in a subject. The skin disorder can be, but is not limited to, acne, psoriasis, eczema, dermatitis (for example, atopic dermatitis and seborrheic dermatitis), fungal infection, viral infection, skin cancer, a precancerous skin lesion (for example, actinic keratosis), a benign skin tumor, a mole, a skin tag, actinic keratosis, diaper rash, *Molluscum contagiosum* and impetigo. Optionally, the skin disorder excludes skin cancer. Thus, any of the compositions set forth herein can be used to manufacture a medicament for the treatment of a skin disorder. For example, any of the compositions set forth herein can be used to manufacture a topical medicament for the treatment of a skin disorder selected from the group consisting of acne, psoriasis, eczema, dermatitis (for example, atopic dermatitis and seborrheic dermatitis), fungal infection, viral infection, skin cancer, a precancerous skin lesion, a benign skin tumor, a mole, a skin tag, actinic keratosis, diaper rash, *Molluscum contagiosum* and impetigo. Optionally, the skin disorder excludes skin cancer.

Provided herein is a method of treating a skin disorder in a subject comprising administering any of the compositions set forth herein to the subject, where the subject has a skin disorder or is at risk of developing a skin disorder. As set forth above, the skin disorder can be, but is not limited to, acne, psoriasis, eczema, dermatitis (for example, atopic dermatitis and seborrheic dermatitis), fungal infection, viral infection, skin cancer, a precancerous skin lesion, a benign skin tumor, a mole, a skin tag, actinic keratosis, diaper rash, *Molluscum contagiosum* or impetigo. Optionally, the skin disorder excludes skin cancer.

Further provided is a method of treating a skin disorder in a subject comprising administering any of the compositions set forth herein to the subject, where the subject has a skin disorder or is at risk of developing a skin disorder. As set forth above, the skin disorder can be, but is not limited to, acne, psoriasis, eczema, dermatitis (for example, atopic dermatitis and seborrheic dermatitis), fungal infection, viral infection, skin cancer, a precancerous skin lesion, a benign skin tumor, a mole, a skin tag, actinic keratosis, diaper rash, *Molluscum contagiosum* or impetigo.

As used herein, the term subject can be a vertebrate, more specifically a mammal (e.g., a human, horse, pig, rabbit, dog, sheep, goat, non-human primate, cow, cat, guinea pig or rodent), a bird, a reptile or an amphibian. The term does not denote a particular age or sex. Thus, adult and newborn subjects, whether male or female, are intended to be covered. As used herein, patient or subject may be used interchangeably and can refer to a subject with a disease or disorder. The term patient or subject includes human and veterinary subjects.

As used herein the terms treatment, treat, treating or ameliorating refers to a method of reducing the effects of a disease or condition or symptom of the disease or condition. Thus, in the disclosed method, treatment can refer to a 10%, 20%, 30%, 40%, 50%, 60%, 70%, 80%, 90%, or 100% reduction or amelioration in the severity of an established disease or condition or symptom of the disease or condition. For example, and not to be limiting, a method for treating a skin disorder is considered to be a treatment if there is a 10% reduction in one or more symptoms of the skin disorder in a subject as compared to a control. For example, the method for treating a skin disorder is considered to be a treatment if there is a 10% reduction in one or more symptoms of the skin disorder in a subject as compared to a control subject that did not receive a composition comprising sandalwood heartwood oil described herein. The control subject can be an untreated subject with a comparable disease or condition or can be the same subject in the absence of the treatment but in the presence of the disorder (i.e., before or after the effective treatment period). Thus, the reduction can be a 10, 20, 30, 40, 50, 60, 70, 80, 90, 100%, or any percent reduction in between 10 and 100 as compared to control levels. It is understood that treatment does not necessarily refer to a cure or complete ablation of the disease, condition, or symptoms of the disease or condition.

For the administration methods disclosed herein, each method can optionally comprise the step of diagnosing a subject with a skin disorder or at risk of developing a skin disorder. The method can also include assessing the effectiveness of the sandalwood oil formulation and modifying the treatment regimen. The methods optionally include the step of altering the treatment based on the responsiveness of the subject.

The sandalwood oil formulations set forth herein can be provided in a pharmaceutical composition. The compositions include a therapeutically effective amount of the cream formulation comprising sandalwood oil in combination with a pharmaceutically acceptable carrier and, in addition, may include other medicinal agents, pharmaceutical agents, carriers, or diluents. Pharmaceutical compositions can be delivered locally to the area in need of treatment, for example, by topical application. Dermal, vaginal and rectal administration is also contemplated.

By pharmaceutically acceptable carrier is meant a material that is not biologically or otherwise undesirable, which can be administered to an individual along with the selected formulation without causing unacceptable biological effects or interacting in a deleterious manner with the other components of the pharmaceutical composition in which it is contained.

The amount of therapeutic agent effective in treating the skin disorder can depend on the nature of the skin disorder and its associated symptoms and can be determined by standard clinical techniques. Therefore, the amounts of sandalwood oil will vary depending on the type of skin disorder. In addition, in vitro assays can be employed to identify optimal dosage ranges. The precise dose to be employed in the formulation will also depend on the seriousness of the disease or disorder and should be decided according to the judgment of the practitioner and each subject's circumstances. The formulations described herein can also be combined with other agents that are utilized to treat a skin disorder.

For example, and not to be limiting, the formulations set forth herein can be combined with other agents utilized to treat acne (for example, adapalene, azelaic acid, benzoyl peroxide, clindamycin, erythromycin, isoretinoin, tetracycline, minocycline, doxycycline, Bactrim/Septra, oral contraceptives, sodium sulfacetamide, tazarotene, tretinoin, sprionolactone, or laser treatment), rosacea (for example, laser treatment, antibiotics or anti-hypertensives), psoriasis (for example, topical steroids, vitamin D analogues, anthralin, topical retinoids, calcinuerin inhibitors, salicylic acid, coal tar, therapeutic antibodies, or light treatment), eczema (for example, topical steroids, pimecrolimus, tacrolimus, light treatment, ciclosporin, azathioprine or methotrexate), dermatitis (for example, aclometasone, hydrocortisone, triamcinolone, clobetasol, betamethasone, mometasone or a glucocorticoid), diaper rash (for example, bufexamac, eosin, topical vitamin A, talc powders or dexpanthenol ointment), fungal infection (for example, fluconazole, voriconazole, itraconazole, ketaconazole, clotrimazole or miconazole), impetigo (mupirocin, fusidic acid, retapamulin, amoxicillin, cephalosporins or macrolides) or *Molluscum contagiosum* (cryotherapy or curettage of lesions).

Ranges may be expressed herein as from about one particular value and/or to about another particular value. When such a range is expressed, this includes from the one particular value and/or to the other particular value. Similarly, when values are expressed as approximations, by use of the antecedent about, it will be understood that the particular value is disclosed.

A number of aspects have been described. Nevertheless, it will be understood that various modifications may be made. Furthermore, when one characteristic or step is described it can be combined with any other characteristic or step herein even if the combination is not explicitly stated. Accordingly, other aspects are within the scope of the claims.

EXAMPLES

Exemplary cream formulations comprising East Indian Sandalwood Oil (EISO) or Rectified East Indian Sandalwood Oil (PISO) were made with and without antioxidants. These formulations were then tested for their ability to maintain pH over three months at a temperature of 40° C. Table 1 provides the components for the formulations and the pH for each formulation at Time Zero, 1 month, 2 months and 3 months. It is understood that, although some of the exemplary cream formulations set forth herein were made with PISO, as described throughout the specification, other sandalwood oils, can be used in combination with an antioxidant, in any of the formulations set forth herein. For example, East Indian (*Santalum album*) sandalwood oil, West Australian sandalwood (*Santalum spicatum*) oil, *Santalum ellipticum*, *S. freycinetianum*, and *S. paniculatum*, or combinations thereof can be used. In other examples, combinations of sandalwood oils comprising East Indian sandalwood (*Santalum album*) oil and West Australian sandalwood (*Santalum spicatum*) oil can be used in the formulations described herein.

Each formulation was made as follows:

1. Prepare the Water Phase (Step A) by adding the water, potassium phosphate monobasic and sodium hydroxide and mix until dissolved. Water is added to achieve a desired volume.
2. Confirm the pH (of #1 above) to ensure pH is between 5.9-6.1.
3. Continue adding remaining ingredients to water phase.
4. Begin heating and mixing Water Phase (Step A) and Oil Phase (Step B) to 70-75° C. until dissolved.
5. Maintain the temperature between 70-75° C. for both phases.
6. While mixing with a dissolver, add Oil Phase (Step B) to Water Phase (Step A). Blend for 5-10 minutes.
7. Change to countermotion/side sweep mixer, and begin cooling batch to below 35° C.
8. Complete by mixing batch with dissolver for 2-5 minutes.

It is understood that the amount of sodium hydroxide, NF can be adjusted depending on the amount of the cream formulation being made. As used herein, "QS" stands for *Quantum Satis* and means to add as much as needed to achieve a desired result This amount can vary, but can be an amount that is added to, for example, bring a formulation to a certain amount or volume, such as 100% w/w.

As shown in Table 1, the pH of the PISO formulation comprising TBHQ was stable over three months at 40° C., as compared to the pH of the PISO formulation that did not comprise an antioxidant and the EISO formulation that did not comprise an antioxidant.

An additional study was performed with other formulations. The design for this study is shown below in Table 2.

TABLE 1

10% EISO VS. PISO Cream with & without Antioxidants

| Components | 10% EISO Cream # 12-0709-03 % w/w | 10% PISO Cream # 12-0829-01 % w/w | 10% PISO Cream w/TBHQ # 12-1010-02 % w/w | 10% Placebo # 12-0829-04 % w/w |
|---|---|---|---|---|
| Water Phase (Step A) | | | | |
| Purified Water, USP | QS | QS | QS | QS |
| Potassium Phosphate Monobasic, NF | 0.418 | 0.418 | 0.418 | 0.418 |
| Sodium Hydroxide, NF | * 0.0142 | * 0.0142 | * 0.0142 | * 0.0142 |
| Sodium Lauryl Sulfate, NF | 1 | 1 | 1 | 1 |
| Propylene Glycol, USP | 0.6 | 0.6 | 0.6 | 0.6 |
| Methylparaben, NF | 0.2 | 0.2 | 0.2 | 0.2 |
| Oil Phase B (Step B) | | | | |
| Cetyl Alcohol, NF | 6 | 6 | 6 | 6 |
| Stearyl Alcohol, NF | 8 | 8 | 8 | 8 |
| Isopropyl Palmitate, NF | 0.25 | 0.25 | 0.25 | 0.25 |
| White Petrolatum, USP | 0.25 | 0.25 | 0.25 | 0.25 |
| Light Mineral Oil, NF | 0.25 | 0.25 | 0.25 | 10.25 |
| Propylparaben, NF | 0.05 | 0.05 | 0.05 | 0.05 |
| t-butyl hydroquinone (TBHQ) | Omit | omit | 0.05 | omit |
| East Indian Sandalwood Oil (EISO) | 10 | omit | omit | omit |
| Rectified East Indian Sandalwood Oil from Australian Grown Trees (PISO) | Omit | 10 | 10 | omit |
| pH @ Time Zero | 5.98 | 5.96 | 5.79 | 6.11 |
| pH 1 month @ 40° C. | 6.04 | 5.82 | 5.80 | 6.05 |
| pH 2 month @ 40° C. | 4.77 | 5.66 | 5.74 | 6.03 |
| pH 3 month @ 40° C. | 3.85 | 5.39 | 5.72 | 6.05 |

TABLE 2

Summary of Design

| Group No | storage temp | Formula | 0 days | 30 days | 60 days | 90 days |
|---|---|---|---|---|---|---|
| 1 | 25 | Base Cream No antioxidant | x | x | x | x |

TABLE 2-continued

Summary of Design

| Group No | storage temp | Formula | 0 days | 30 days | 60 days | 90 days |
|---|---|---|---|---|---|---|
| 2 | 40 | Base Cream No antiOxidant | | x | x | x |
| 3 | 25 | Base w/0.05% TBHQ | x | x | x | x |
| 4 | 40 | Base w/0.05% TBHQ | | x | x | x |
| 5 | 25 | Base w/2% Botanessentials | x | x | x | x |
| 6 | 40 | Base w/2% Botanessentials | | x | x | x |
| 7 | 25 | Base w/0.5% Rosamox | x | x | x | x |
| 8 | 40 | Base w/0.5% Rosamox | | x | x | x |
| 9 | 25 | Base w/TBHQ, Botanes, Rosamox | x | x | x | x |
| 10 | 40 | Base w/TBHQ, Botanes, Rosamox | | x | x | x |

Samples tested for pH and appearance only Package in 2 oz. Clear Glass Jars & monitor monthly or 2X monthly?

As shown in Table 3, a cream formulation comprising 10% PISO without an antioxidant was not stable over time, at 25° C. or 40° C.

TABLE 3

Results

10% PISO Cream Base- 6X Conc. Buffer NO Antioxidants Added
Lot Code 12-1010-01

| Date Tested | Note pH & Appearance Only | |
|---|---|---|
| Initial Oct. 10, 2012 | 5.83 | |
| Oct. 11, 2012 | 5.87 | |
| Temperatures | 25° C. | 40° C. |
| Oct. 23, 2012 (2 weeks) | 5.87 | 5.86 |
| Nov. 8, 2012 (1 month) | 5.83 | 5.78 |
| Nov. 21, 2012 (1.5 months) | 5.78 | 5.74 |
| Dec. 10, 2012 (2 months) | 5.64 | 5.62 |
| Jan. 4, 2013 (3 months) | 5.58 | 5.51 |
| Feb. 5, 2013 (4 months) | 5.56 | 5.16 |
| Mar. 6, 2013 (5 months) | 5.51 | 4.61 |

As shown in Table 4, the pH of a cream formulation comprising 10% PISO and 0.05% TBHQ was stable over five months, at 25° C. or 40° C. This formulation was still stable over eight months at 25° C. or 40° C.

TABLE 4

10% PISO Cream Base- 6X Conc. Buffer + 0.05% TBHQ
Lot Code 12-1010-02

| Date Tested | Note pH & Appearance Only | |
|---|---|---|
| Initial Oct. 10, 2012 | 5.79 | |
| Oct. 11, 2012 | 5.85 | |
| Temperatures | 25° C. | 40° C. |
| Oct. 23, 2012 (2 weeks) | 5.84 | 5.83 |
| Nov. 8, 2012 (1 month) | 5.84 | 5.80 |
| Nov. 21, 2012 (1.5 months) | 5.80 | 5.77 |
| Dec. 10, 2012 (2 months) | 5.81 | 5.74 |
| Jan. 4, 2013 (3 months) | 5.82 | 5.72 |
| Feb. 5, 2013 (4 months) | 5.83 | 5.70 |
| Mar. 6, 2013 (5 months) | 5.86 | 5.62 |

As shown in Table 5, the pH of a cream formulation comprising 10% PISO and 2% Botanessentials RSST was stable over five months at 25° C., but not at 40° C.

TABLE 5

10% PISO Cream Base- 6X Conc. Buffer + 2% Botanessentials RSST Lot Code 12-1010-03

| Date Tested | Note pH & Appearance Only | |
|---|---|---|
| Initial Oct. 10, 2012 | 5.87 | |
| Oct. 11, 2012 | 5.93 | |
| Temperatures | 25° C. | 40° C. |
| Oct. 23, 2012 (2 weeks) | 5.90 | 5.90 |
| Nov. 8, 2012 (1 month) | 5.92 | 5.82 3+ oil droplets present on surface |
| Nov. 21, 2012 (1.5 months) | 5.92 | 5.81 3+ oil droplets present on surface |
| Dec. 10, 2012 (2 months) | 5.93 | 5.80 |
| Jan. 4, 2013 (3 months) | 5.91 | 5.81 oil droplets present on surface |
| Feb. 5, 2013 (4 months) | 5.91 | 5.75 Slight separation present |
| Mar. 6, 2013 (5 months) | 5.93 | 5.77 Slight separation present |

As shown in Table 6, the pH of a cream formulation comprising 10% PISO and 0.5% Rosamax was stable over five months, at 25° C. and 40° C. This formulation was still stable over eight months at 25° C. or 40° C.

TABLE 6

10% PISO Cream Base- 6X Conc. Buffer + 0.5% Rosamox
Lot Code 12-1010-04

| Date Tested | Note pH & Appearance only | |
|---|---|---|
| Initial Oct. 10, 2012 | 5.80 | |
| Oct. 11, 2012 | 5.85 | |
| Temperatures | 25° C. | 40° C. |
| Oct. 23, 2012 (2 weeks) | 5.80 | 5.81 |
| Nov. 8, 2012 (1 month) | 5.81 | 5.70 |
| Nov. 21, 2012 (1.5 months) | 5.78 | 5.73 |
| Dec. 10, 2012 (2 months) | 5.77 | 5.74 |
| Jan. 4, 2013 (3 months) | 5.81 | 5.69 |
| Feb. 5, 2013 (4 months) | 5.79 | 5.65 |
| Mar. 6, 2013 (5 months) | 5.82 | 5.65 |

As shown in Table 7, a pH of a cream formulation comprising 10% PISO and 0.05% TBHQ, 0.5% Rosamax and 2% Botanessentials RSST was stable over five months at 25° C., but not at 40° C.

TABLE 7

10% PISO Cream Base- 6X Conc. Buffer 0.05% TBHQ 2% Botanessentials 0.5% Rosamox Lot Code 12-1010-05

| Date Tested | Note pH & Appearance Only | |
|---|---|---|
| Initial Oct. 10, 2012 | 5.90 | |
| Oct. 11, 2012 | 5.93 | |
| Temperatures | 25° C. | 40° C. |
| Oct. 23, 2012 (2 weeks) | 5.88 | 5.91 |
| Nov. 8, 2012 (1 month) | 5.89 | 5.89 2-3 oil droplets present on surface |
| Nov. 21, 2012 (1.5 months) | 5.88 | 5.86 2-3 oil droplets present on surface |
| Dec. 10, 2012 (2 months) | 5.81 | 5.74 oil droplets present on surface |
| Jan. 4, 2013 (3 months) | 5.83 | 5.69 oil droplets present on surface |
| Feb. 5, 2013 (4 months) | 5.88 | 5.73 slight separation present |
| Mar. 6, 2013 (5 months) | 5.86 | 5.74 separation present on surface |

FIG. 1 provides a graphical representation of the data set forth in Tables 3-7.

Figure 2:
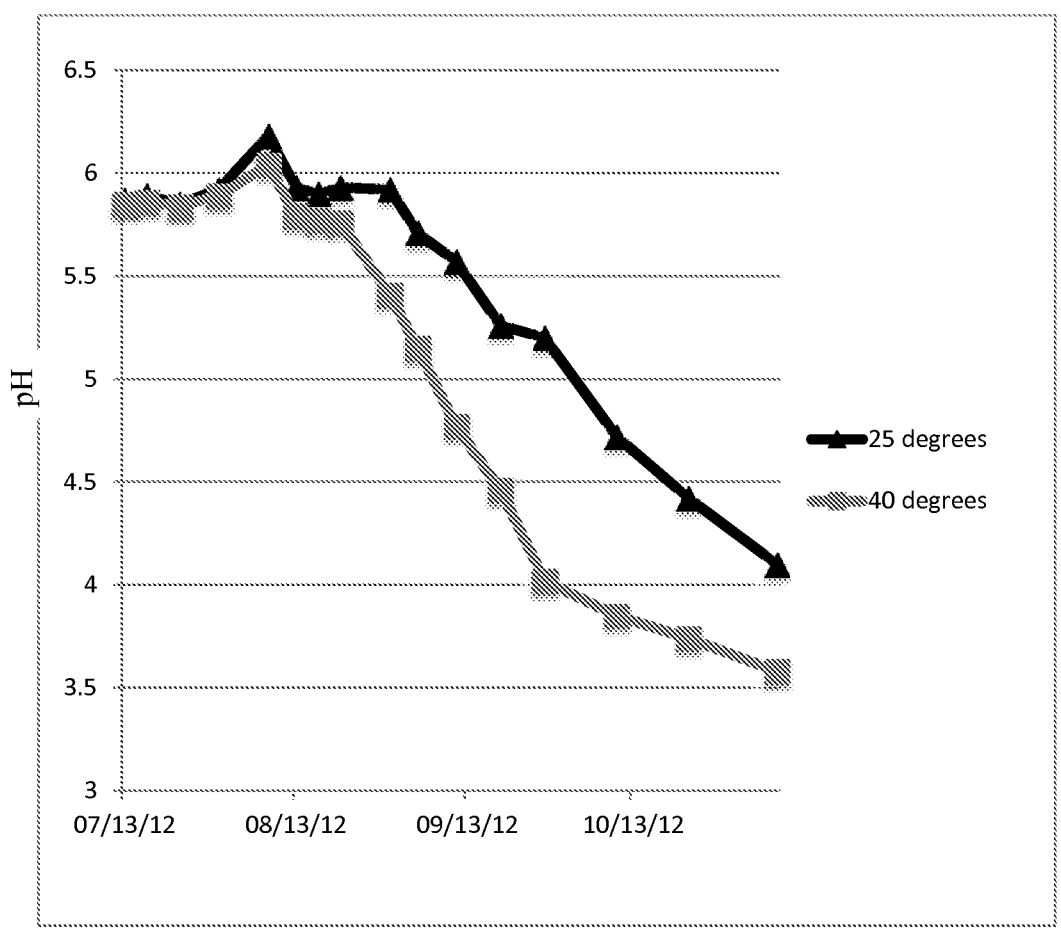
FIG. 2 is a graph showing the decrease in pH of a cream formulation comprising sandalwood oil, wherein the formulation does not comprise an antioxidant.

As shown in Table 8, the pH of a cream formulation comprising sandalwood oil and phosphate buffer, without an antioxidant, was not stable over time. FIG. 2 is a graphical representation of this data.

TABLE 8

| | buffer; no antioxidant | |
|---|---|---|
| Date Tested | 25° C. | 40° C. |
| Jul. 13, 2012 | 5.87 | 5.85 |
| Jul. 17, 2012 | 5.89 | 5.86 |
| Jul. 23, 2012 | 5.85 | 5.84 |
| Jul. 30, 2012 | 5.92 | 5.89 |
| Aug. 8, 2012 | 6.18 | 6.04 |
| Aug. 13, 2012 | 5.93 | 5.79 |
| Aug. 17, 2012 | 5.9 | 5.77 |
| Aug. 21, 2012 | 5.93 | 5.76 |
| Aug. 30, 2012 | 5.92 | 5.41 |
| Sep. 4, 2012 | 5.71 | 5.15 |
| Sep. 11, 2012 | 5.57 | 4.77 |
| Sep. 19, 2012 | 5.26 | 4.46 |
| Sep. 27, 2012 | 5.2 | 4.02 |
| Oct. 10, 2012 | 4.72 | 3.85 |
| Oct. 23, 2012 | 4.42 | 3.74 |
| Nov. 8, 2012 | 4.1 | 3.58 |

In addition to the formulations set forth in Table 1 comprising 10% sandalwood oil and an antioxidant, additional exemplary formulations comprising an antioxidant and 2.5% or 5% sandalwood oil are set forth in Table 9.

TABLE 9

| Components | 2.5% Cream # 13-0129-02 % w/w | 5% Cream — % w/w | 10% Cream # 12-1010-02 % w/w | Placebo # 13-0129-01 % w/w |
|---|---|---|---|---|
| Water Phase (Step A) | | | | |
| Purified Water, USP | 72.9178 | 72.9178 | 72.9178 | 72.4178 |
| Potassium Phosphate Monobasic, NF | 0.418 | 0.418 | 0.418 | 0.418 |
| Sodium Hydroxide, NF | * 0.0142 | * 0.0142 | * 0.0142 | * 0.0142 |
| Sodium Lauryl Sulfate, NF | 1 | 1 | 1 | 1 |
| Propylene Glycol, USP | 0.6 | 0.6 | 0.6 | 0.6 |
| Methylparaben, NF | 0.2 | 0.2 | 0.2 | 0.2 |
| Oil Phase B (Step B) | | | | |
| Cetyl Alcohol, NF | 6 | 6 | 6 | 6 |
| Stearyl Alcohol, NF | 8 | 8 | 8 | 8 |
| Isopropyl Palmitate, NF | 0.25 | 0.25 | 0.25 | 0.25 |
| White Petrolatum, USP | 0.25 | 0.25 | 0.25 | 0.25 |
| Light Mineral Oil, NF | 7.75 | 5.25 | 0.25 | 10.25 |
| Propylparaben, NF | 0.05 | 0.05 | 0.05 | 0.05 |
| t-butyl hydroquinone (TBHQ) | 0.05 | 0.05 | 0.05 | 0.05 |
| Fragrance # SD-468 (Synthetic Sandalwood Fragrance) from Creative Fragrances | N/A | N/A | N/A | 0.5 |
| Rectified East Indian Sandalwood Oil from Australian Grown Trees (PISO) | 2.5 | 5 | 10 | Omit |

Each formulation was made as follows:
1. Prepare the Water Phase (Step A) by adding the water, potassium phosphate monobasic and sodium hydroxide and mix until dissolved. Water is added to achieve a desired volume.
2. Confirm the pH (of #1 above) to ensure pH is between 5.9-6.1.
3. Continue adding remaining ingredients to water phase.
4. Begin heating and mixing Water Phase (Step A) and Oil Phase (Step B) to 70-75° C. until dissolved.
5. Maintain the temperature between 70-75° C. for both phases.
6. While mixing with a dissolver, add Oil Phase (Step B) to Water Phase (Step A). Blend for 5-10 minutes.
7. Change to countermotion/side sweep mixer, and begin cooling batch to below 35° C. Fragrance in the placebo formulations were added below 40° C., with a minimum of 30 minutes of stirring.
8. Complete by mixing batch with dissolver for 2-5 minutes.

It is understood that the amount of sodium hydroxide, NF can be adjusted depending on the amount of the cream formulation being made.

Cream formulations comprising 2.5% PISO and 0.05% TBHQ, or 5% PISO and 0.05% TBHQ are also stable over time at 25° C. or 40° C.

What is claimed is:

1. A stabilized cream formulation for treating a skin disorder comprising effective amounts of:
   a) Sandalwood oil;
   b) one or more antioxidants; and
   c) a phosphate buffer,
   wherein the concentration of the one or more antioxidants is from about 0.03% (w/w) to about 0.5% (w/w), wherein the pH of the formulation is between about 4 and about 6; and wherein the one or more antioxidants are selected from the group consisting of t-butyl hydroquinone (TBHQ) and rosemary extract.

2. The formulation of claim 1, wherein the sandalwood oil is from *Santalum album* or *Santalum spicatum* or a combination thereof.

3. The formulation of claim 1, wherein the concentration of the sandalwood oil is from about 0.3% (w/w) to about 10% (w/w).

4. The formulation of claim 1, wherein the concentration of the one or more antioxidants is from about 0.05% (w/w) to about 0.1% (w/w).

5. The formulation of claim 1, wherein the phosphate buffer is monobasic potassium phosphate buffer or dibasic potassium phosphate buffer.

6. The formulation of claim 1, wherein the concentration of the phosphate buffer is from about 0.4% (w/w) to about 10% (w/w).

7. The formulation of claim 1, wherein the formulation further comprises a solvent.

8. The formulation of claim 7, wherein the solvent is water.

9. The formulation of claim 1, wherein the formulation further comprises one or more pharmaceutically acceptable excipients.

10. A method of treating a skin disorder in a subject comprising administering a therapeutically effective amount of a formulation of claim 1 to the subject, wherein the subject has a skin disorder or is at risk of developing a skin disorder wherein the skin disorder is selected from the group consisting of acne, psoriasis, eczema, dermatitis, fungal infection, actinic keratosis, diaper rash, *Molluscum contagiosum* and impetigo.

11. The method of claim 10, wherein the formulation is administered topically.

12. The formulation of claim 1, wherein the sandalwood oil does not comprise an ester derivative of santalol.

13. The formulation of claim 12, wherein the santalol is an alpha-santalol.

14. The formulation of claim 12, wherein the santalol is a beta-santalol.

* * * * *